United States Patent [19]
Harris

[11] Patent Number: 5,990,154
[45] Date of Patent: Nov. 23, 1999

[54] ANTI-FIRST-PASS EFFECT COMPOUNDS AND CITRUS EXTRACT

[75] Inventor: James W. Harris, Cocoa Beach, Fla.

[73] Assignee: Bioavailability Systems, L.L.C., Cocoa Beach, Fla.

[21] Appl. No.: 09/082,939

[22] Filed: May 22, 1998

Related U.S. Application Data

[60] Provisional application No. 60/048,183, May 30, 1997.
[51] Int. Cl.$^6$ .......................... A23L 1/212; A61K 31/35; A61K 35/79; C07D 493/04
[52] U.S. Cl. .................. 514/453; 424/195.1; 426/330.5; 426/333; 426/616; 549/264; 549/282
[58] Field of Search .......................... 424/195.1; 514/453

[56] References Cited

U.S. PATENT DOCUMENTS 5,820,915  10/1998  Harris .

*Primary Examiner*—Robert W. Ramsuer
*Assistant Examiner*—Taofiq A Solola
*Attorney, Agent, or Firm*—Oblon, Spivak, McClelland, Maier & Neustadt, P.C.

[57] ABSTRACT

This invention relates to the process of making citrus (preferably grapefruit) extract having reduced levels of phototoxic furocoumarins and containing enhanced amounts of one or more anti-first pass effect compounds.

2 Claims, 6 Drawing Sheets

ANTI-FIRST-PASS EFFECT COMPOUNDS AND CITRUS EXTRACT

This application is a regular application of provisional application 60/048,183, filed May 30, 1997.

BACKGROUND OF THE INVENTION

1. Field of the Invention

The present invention relates to anti-first-pass effect fractions, compounds, etc. The invention also relates to a citrus (most preferably grapefruit) extract, oil, concentrate, juice, by-product, etc. having reduced levels as compared to naturally-occurring levels of phototoxic furocoumarins and/or containing enhanced amounts over naturally-occurring amounts of one or more invention anti-first-pass effect compounds. Preferably, the invention compounds and extracts are provided as a dietary supplement or as a medical food or as some other type of food product, or as a drug, pharmaceutical or drug preparation, or in some other physical form, and that they, in addition to any other function they have, if any, function as an inhibitor of the first-pass effect of orally-administered drugs. The most preferred embodiment of the invention relates to particular chemical species which inhibit the first-pass effect.

2. Discussion of the Background

The "first-pass effect" of drugs given orally refers to the process of drug degradation during a drug's transition from initial ingestion to circulation in the blood stream. Often discussed in terms of "bioavailability", it is not uncommon for a drug that is administered to a patient orally to be given in a 5-fold or greater amount than ultimately necessary due to the degradation that occurs in the patient's body after intake. For example, the impact of the first-pass effect can be demonstrated with the case of the antihistamine terfenadine, wherein 99.5% of a tablet given by mouth is quickly changed to metabolites; hence, the bioavailability of terfenadine is approximately 0.5% (D. Garteiz et al., Arzneim.-Forsch., 1982; 32:1185–1190). As a further example, cyclosporin A, administered to organ transplant patients, has a median oral bioavailability of approximately 30% and a bioavailability range of approximately 8–92% among patients. Because of this large interindividual variation in cyclosporin bioavailability, frequent monitoring of blood concentrations during therapy initiation is necessary.

The inhibition of a particular xenobiotic metabolism as a mechanism of action generally, as well as the inhibition of the first-pass effect with chemical agents specifically, is well known in the art and has been for some time. Examples include the treatment of methanol (wood alcohol) poisoning with ethanol and the inhibition of the first-pass effect of cyclosporin with ketoconazole. See, for example, First, R. M. et al., The Lancet, 1198, Nov. 18, 1989, incorporated herein by reference.

Although the agent(s), enzyme type(s), biological processes' etc. responsible for the first-pass effect have not been fully identified, research has focused on agents capable of inhibiting the cytochrome P450 system. Inhibition of the P450 system is a model for in vitro determination of in vivo bioavailability enhancement. See, e.g., U.S. Pat. Nos. 5,478,723 and 5,567,592, both incorporated herein by reference for a more full description of the P450 system. As reported by A. Keogh et al. (N. Eng. J. Med., Vol. 333, No. 10, p. 628, 1995) and S. Butman et al. (J. Heart Lung Transpl., Vol. 10, No. 3, 1991), the dose of cyclosporin required by heart transplant patients could be reduced by approximately 85% when cyclosporin was co-administered with ketoconazole. In economic terms, both references estimated cost savings to be equal to approximately $5,000 per year per patient. Other drugs which are subject to the first-pass effect and whose bioavailability is increased by inhibitors commonly given to humans include midazolam (K. Olkkola et al, Clin. Pharmacol. Ther., 1993, 53:298–305), terfenadine (Seldane) (P. Honig et al., JAMA, Vol. 269, No. 12, 1513, 1993) and triazolam (Varhe, A. et al, Clin. Pharmocol. Ther., 1994, 56:601–7).

In addition to ketoconazole, the drugs fluconazole, ritonavir, itraconazole, miconazole, erythromycin and troleandomycin have been identified as inhibitors of the first-pass effect. These compounds, however, are antiviral, antimicrobial, or antifungal agents. Because of the heightened current awareness of the fact that overuse of such agents can result in resistant microbial strains, because some of the most effective inhibitors are antimicrobials, and because transplant and HIV-infected patients have compromised immune systems, the use of these inhibitors of the first-pass effect has significant drawbacks and, for example, in the case of ketoconazole, the purposeful coadministration of this inhibitor with drugs susceptible to the first-pass effect has not become widespread. In fact, the emergence of antifungal drug resistance in immunocompromised patients is already known (T. J. Walsh: "Emergence of Antifungal Drug Resistance in Immunocompromised Patients" Seminar, National Institutes of Health, Feb. 7, 1996; Georgopapadakou, N. H. et al, Antimicrobial Agents and Chemotherapy, February 1996, p. 279–291).

In 1991, Bailey et al. reported (Bailey, D. G., et al, The Lancet, Vol. 337, Feb. 2, 1991, p. 268, incorporated herein by reference) that grapefruit juice increased the bioavailability of felodipine, and indicated that the inhibition of cytochrome P450 enzymes by bioflavonoids could explain their findings. This identification of bioflavonoids as the active ingredient in grapefruit juice was immediately challenged by R. Chayen et al. (The Lancet, Vol. 337, Apr. 6, 1991, p. 854) who suggested that susquiterpenoid compounds rather than flavonoids were the active ingredients in grapefruit juice responsible for inhibition of the first-pass effect. Although Bailey and Edgar were granted a patent (U.S. Pat. No. 5,229,116, incorporated herein by reference) directed to a method of increasing the bioavailability of a pharmaceutical agent by co-administration of a flavonoid such as naringin, their own recent work has openly brought into question the accuracy of their initial identification of flavonoids as active ingredient. See, for example, Bailey et al., Clin. Pharmacokinet. 26 (2):91–98, 1994, particularly pages 95 and 96 thereof. See also Edwards, D. J. et al, Life Sciences, Vol. 59, No. 13, pp. 1025–130, 1996.

The reported effects of grapefruit juice as an effective inhibitor of the first-pass effect has lead to numerous research articles regarding the inhibition of the first-pass effect by grapefruit juice on, e.g., nifedipine, nitrendipine, nisoldipine, cyclosporin A, midazolam, triazolam, coumarin, and caffeine. As these results have become better known, the so-called "grapefruit juice effect" has become the subject of newspaper articles, newsletters and medical texts intended for the general public. See, for example, "The Medical Letter", Vol. 37 (issue 955) Aug. 18, 1995, *The Peoples Pharmacy,* Chapter 4 (St. Martin's Press) 1996, p. 41, the Feb. 19, 1991 newspaper article regarding felodopine and grapefruit juice in the New York Times (section C, page 3, column 1)) and a recent article in the Washington Post (Section A, p. 11, 8/30/96).

A review of the published studies that demonstrate the grapefruit juice effect also shows that the magnitude of the effect appears to be related to the source of the juice. In fact, the production of commercial citrus juice involves a complicated series of factors that increase the variability of the final product's composition. These factors include the squeezing technique, the concentration technique, the origin of the fruit, the ripeness of the fruit at harvest, the admixture of fruits differing in origin and ripeness, the admixture of juice and fruit tailings, etc. Because the active agents in the grapefruit juice that inhibit the first-pass effect were heretofore unknown or misidentified, scientists and consumers could not choose a grapefruit juice preparation and rely upon its utility to inhibit the first-pass effect.

Moreover, grapefruit juice in particular and citrus products in general are known to contain phototoxic furocoumarin derivatives including psoralen, xanthotoxin and bergapten. While these compounds are useful for the controlled, clinical treatment of selected dermatological diseases including vitiligo, psoriasis and mycosis fungoides, they are also known to be toxic, in particular, phototoxic. The structure-activity relationship for the phototoxicity of furocoumarins has been clearly delineated from human studies (for example, L. Musajo et al, Herba Hungarica, 1971, Tom. 10, No. 2–3, pp. 79–94), and these studies show that photosensitizing activity is removed by ring hydroxylation or by lengthening the alkyl-chain length of ether substituents.

Careful evaluation of the literature shows that psoralen and certain low carbon number ether substituted furocoumarins that are given to humans in large doses do inhibit cytochrome P450. See, for example, D. Bickers et al., J. Investigative Dermatology, 79:201–205, 1982, M. Tinel et al., Biochemical Pharmacology, Vol. 36, No. 6, 951–955, 1987, H. Fouin-Fortunet et al., J. Pharm. Experimental Therapeutics, Vol. 236, No. 1, 237–247, 1986, and D. Mays et al, Clin. Pharmacol. Ther., 42:621–626, 1987. Thus, and because the known successful inhibitors of the first-pass effect generally inhibit cytochrome P450, a tempting conclusion, particularly in view of the recent disclaimers by Bailey, and others, is that it is these low molecular weight furocoumarins present in citrus that are the active first-pass inhibitors in grapefruit juice. In fact, and as will be described more fully below with regard to the present invention, the present inventor has found that this is not the case, and that it is now possible to produce a citrus product or pharmaceutical composition that both inhibits the first-pass effect and that contains no or reduced amounts of low molecular weight phototoxic furocoumarins.

OBJECTS OF THE PRESENT INVENTION

It is one object of this invention to provide a citrus-based (preferably lime- or grapefruit-based or derived) composition that inhibits the first-pass effect and that, optionally, is free of or contains a reduced amount (as compared to a naturally occurring amount) of phototoxic and, optionally, non-first-pass inhibiting low molecular weight furocoumarins.

Another object of the present invention is to provide a citrus-, preferably lime- or grapefruit-based composition that is effective against the first-pass effect.

Another object of the present invention is to provide a citrus-, preferably lime- or grapefruit-based composition that contains no, or reduced amounts as compared to naturally occurring, of phototoxic low molecular weight furocoumarins.

Another object of the present invention is to provide a citrus-, preferably lime- or grapefruit-based composition with consistent and reliable first-pass inhibiting activity.

Another object of the present invention is to provide the above-described compositions as a component of products that provide active ingredients, therapeutic agents, drugs, etc. or other substances that are subject to the first-pass effect in humans.

Another object of the present invention is to provide first-pass effect inhibiting compounds, also called bioenhancers and inhibitors herein.

Another object of the present invention is to provide mixtures of one or more invention first-pass effect inhibiting compounds with various therapeutic agents, active agents, drugs or other substances (hereinafter referred to as "drugs") that are subject to the first-pass effect.

Another object of the present invention is the provision of a method for inhibiting the first-pass effect in patients taking drugs having a first-pass effect.

Another object of the present invention is a method for preparing the abovedescribed compositions, compounds and mixtures.

Another object of the present invention is a method for preparing a citrus-based composition containing no or reduced amounts as compared to naturally occurring amounts of phototoxic and non-first-pass inhibiting furocoumarins preferably using reagents that the U.S. Food and Drug Administration regards may be used for food or drug manufacturing including GRAS materials. In this application, "non-first-pass inhibiting" includes first-pass activity provided by 2000 nM bergamottin and imperatorin according to Protocol C herein.

Another object of the invention is to provide and use first-pass effective compounds and compositions containing such compounds in isolated form and/or pyrogen-free form and/or sterile form and/or substantially pure form and/or pharmaceutical form and/or chemically pure form. These forms, as their names specify, are different from the invention compounds as they naturally occur in citrus and citrus products such as juice, commercially available juice concentrates, etc.

Another object of the invention is to provide a method of inhibiting the first-pass effect by administration of the above compounds and compositions to humans.

These and other objects will become apparent to those of ordinary skill in this art upon a full appreciation of the invention as described below with regard to preferred embodiments.

DETAILED DESCRIPTION OF THE PREFERRED EMBODIMENTS

The present inventor has discovered that phototoxic low molecular weight furocoumarins and certain ether-substituted furocoumarins that are naturally present in citrus extracts, juices, by products, etc. may be removed therefrom or reduced in concentration without destroying the first-pass effect inhibiting characteristics thereof In addition, the present inventor has discovered a method for preparing such citrus-based compositions using only FDA or USP acceptable reagents. Further, the present inventor has correctly isolated active fractions present in citrus-based compositions that are responsible for the inhibition of the first-pass effect. The present invention has been completed on the basis of these findings and will be described in more detail below.

The citrus-based compositions of the present invention contain at least one first-pass effective citrus-derived fraction, extract, concentrate, peel, juice, oil, by-product, etc., (hereinafter referred to as the citrus-derived substance) and may be provided by any combination of these forms and may be derived from more than one citrus fruit. Useful citrus fruits herein include grapefruit, lemon, lime and any citrus fruit containing a first-pass effect inhibiting compound or mixture of compounds. Prior work in the field indicates that a common type of orange (Citrus sinensis) does not inhibit the first-pass effect. Citrus fruits that contain one or more substances that inhibit the first-pass effect are included in the invention, including all cross breeds, etc. and are referred to herein as "first-pass citrus". A preferred citrus fruit useful in the present invention is grapefruit. First-pass effective materials described herein are materials that prevent or retard the degradation of orally administered drugs in the body. Preferably, the first-pass effective materials of the invention, including invention fractions, increase drug bioavailability by at least 1%, preferably by more than 5% and most preferably by more than 15% including 20, 25, 30, 35, 40, 45, 50, 55, 60, 65, 70, 75, 80, 85, 90, 100, 150, 200, 250, 300, etc. percent as measured by the Area Under the Curve (AUC) method. See U.S. Pat. No. 5,567,592 incorporated herein by reference. A several-fold, including 5, 10, 15, 20-fold, etc. increase in bioavailability (i.e., several hundreds or thousands of percent AUC increase) is not unusual with the present invention.

Preferred citrus-derived substances of the invention include cold-pressed citrus oil, particularly cold-pressed grapefruit, lime, lemon, etc., oil, and citrus by-products including tailings from citrus packing/juice plants. Cold-pressed citrus oils, including cold-pressed orange (except Citrus sinensis), grapefruit, lime and lemon oil, are commodities and are described, for example, in the Food Chemicals Codex, Fourth Edition, National Academy Press, Washington, D.C. 1996, incorporated herein by reference. Other citrus-derived substances useful herein include the various other citrus oils (distilled, essential, desert type, etc.), bitter cold-pressed oils, etc. Geographical origin of the invention citrus providing the citrus-derived substance is unimportant herein. Citrus juices or peel (rind) may also be used, as well as any first-pass effective solid, semi-solid or liquid portion of a first-pass citrus. Mixtures may be used.

The citrus-derived substance of the present invention compositions may make up the entire citrus-based composition or may be only a part thereof. Food grade or pharmaceutically acceptable diluents, excipients, carriers, etc., may be added, if desired.

The citrus-derived substance of the present invention composition is preferably treated so as to reduce the amount of phototoxic and, optionally, non-first-pass effective, furocoumarins naturally present therein. Preferably, these furocoumarins are completely removed, meaning that they are removed to an extent such that their presence is undetectable by liquid and, preferably, gas chromatography.

The invention method for removing phototoxic low molecular weight furocoumarins from invention citrus-derived components preferably comprises optional removal of volatile components (components removed after 12–24 h at a pressure of $10^{-2}$ $10^{-3}$ Torr) and extraction with mixtures of at least one $C_1$–$C_{10}$ alcohol (preferably ethanol) and water, optionally in the presence of base. The extraction mixture of alcohol and water is discarded and what is left is useful herein. $C_2$–$C_5$ alcohols are also preferred as are $C_2$ and $C_3$ and $C_4$ alcohols. The alcohol (ethanol) may either be 100% alcohol or may be conveniently supplied and used in commonly available alcohol-water dilutions (e.g., 95% ethanol/5% water, etc.). In all cases the alcohol (ethanol) reagent is preferably U.S.P. grade or better. The water used herein for extracting the invention citrus-derived substance (component) is preferably distilled water, and is also preferably U.S.P. grade or better. Any combination of solvents or single solvent may be used herein for extraction. The solvent(s) are preferably FDA acceptable for food and drug manufacturing.

The present invention method for removing phototoxic low molecular weight furocoumarins may include successive extractions with alcohol (ethanol)/water mixtures, and the successive alcohol (ethanol)/water mixtures used may either be of the same volume ratio or different volume ratios. Preferred alcohol (ethanol):water volume ratios range from 1:10–10:1, are more preferably 1:1 (±3%, 5%, 8% or 10%) and may be 45–60% alcohol (ethanol) on a volume/volume basis, and include 2:1, 3:1, 1:2, 1:3, etc. as well as 55/45, 60/40, 65/35, 70/30, 45/55, 40/60, 35/65, 30/70, etc. The extractions may be accomplished by any method known in the art including liquid-liquid extraction, liquid-solid extraction, etc. When the raw material used to prepare the invention citrus-derived extract is, for example, an oil, the alcohol (ethanol)/water mixture used for extraction can be simply added thereto, shaken therewith, and separated naturally or with the help of a centrifuge. Repeated extraction is helpful, as are continuous extraction methods such as countercurrent extraction, etc.

Preferably, the invention method for removing phototoxic low molecular weight furocoumarins significantly diminishes, and preferably completely removes beyond the detection limits of liquid and, preferably, gas chromatography, methoxy-substituted linear and angular furocoumarins including xanthotoxin (8-methoxypsoralen), bergapten (5-methoxypsoralen), isobergapten, isopimpinellin, etc., and unsubstituted linear and angular furocoumarins (psoralen, angelicin, etc.). Furocoumarins that have been determined herein to be ineffective first-pass effect furocoumarins may also be removed, if desired. These compounds include bergamottin, psoralen, angelicin, isopimpinellin and imperatorin.

The use of present invention citrus-derived substance, compositions, mixtures, inhibitors, compounds, etc. are not limited and may preferably be administered in amounts of 2 nanograms- 2 g and more per patient per day to increase the bioavailability of drugs taken orally by a patient. Compositions of the invention contain, preferably, more of the invention compounds than naturally present in citrus products. Dosages are determinable by those of ordinary skill in the art and depend upon the extent to which a, e.g., active agent (drug) is subject to the first-pass effect, etc. The invention citrus-derived substance, compositions, mixtures and compounds may optionally be part of or added to a citrus-based composition or other edible material which is preferably a tastemasking flavor, juice, etc. The citrus-derived substance, mixtures, compositions and compounds of the invention inhibit the first-pass effect of drugs taken orally by humans and other animals. A "first-pass effective amount" of an invention material is any amount which reduces the first-pass effect of any substance by any amount (e.g., 1%, 5%, 10%, etc.; see above where the AUC method is described, including all values and ranges between these values) as compared to the case where no invention material is administered. A "first-pass effective" invention citrus-derived substance, mixture, composition or compound is a material that inhibits the observed first-pass effect of at least one drug, preferably the first-pass effect caused by the cytochrome P450 system. This is also referred to herein as anti-first-pass activity. Administration is preferably co-administration, meaning just before, just after, or with drug, active agent, therapeutic agent, medical food subject to the first-pass effect, etc. "Just before" and "just after" include all times where the invention material provides a benefit by inhibiting the first-pass effect. Preferred forms of the invention comprise the invention citrus-derived substance, mixture, composition or dimer inside of, e.g., a gel capsule, or co-formulated with food-grade or pharmaceutically-acceptable binders, diluents, etc. Dosage forms (salt or base, tablet or gum, etc.) as well as binders, salt forms, excipients, etc. usefull are found in, e.g., U.S. Pat. Nos. 5,576,448, 5,576,446, 5,576,437, 5,576,439, 5,576,438, 5,576,337, 5,576,339 and 5,576,336, all incorporated herein by reference. The invention citrus-derived substance, mixtures, compositions and fractions are preferably provided in an amount that provides consistent, reliable potency from batch to batch regardless of the form in which it is provided.

The word "drug" as used herein is defined as a chemical capable of administration to an organism which modifies or alters the organism's physiology. More preferably the word "drug" as used herein is defined as any substance intended for use in the treatment or prevention of disease, particularly for humans. Drug includes synthetic and naturally occurring toxins and bioaffecting substances as well as recognized pharmaceuticals, such as those listed in "The Physicians Desk Reference," 47th edition, 1993, pages 101–321; "Goodman and Gilman's The Pharmacological Basis of Therapeutics" 8th Edition (1990), pages 84–1614 and 1655–1715; and "The United States Pharmacopeia, The National Formulary", USP XXII NF XVII (1990), the compounds of these references being herein incorporated by reference. The term drug also includes compounds that have the indicated properties that are not yet discovered or available in the U.S. The term drug includes pro-active, activated and metabolized forms of drugs. The present invention can be used with drugs consisting of charged, uncharged, hydrophilic, zwitter-ionic, or hydrophobic species, as well as any combination of these physical characteristics. A hydrophobic drug is defined as a drug which in its non-ionized form is more soluble in lipid or fat than in water. Preferably, a hydrophobic drug is defined as a drug more soluble in octanol than in water. See U.S. Pat. No. 5,567,592, incorporated herein by reference.

The present invention citrus-derived substance may be co-formulated with drugs, preferably drugs that are subject to the first-pass effect. Preferably the drug has an oral bioavailability of 90% or less, more preferably 50% or less. Examples include, in addition to those incorporated by reference above, ritonavir, saquinavir, indinavir, L-deprenyl, tacrolimus, cyclosporin A (Sandimmune®), cyclosporin A (Neoral®), nelfinavir, VX-478/141W94, felodipine, nifedipine and sumatriptan. Such co-formulations include the invention citrus-derived substance and/or one or more compounds in amounts mentioned above with, typically, lesser amounts than currently necessary of drug active ingredients that are subject to the first-pass effect. Binders, diluents, etc. acceptable for pharmaceutical use can also be added. One of ordinary skill in the art is capable of determining the dosage of the invention citrus-derived substance and/or dimer and drug active ingredient based on simple testing procedures well known in the art and including pharmacological experiments which determine the amount of drug in the blood stream over a given time period after administration.

Other products useful for co-formulation herein are any and all drug, medical food, or other products that are subject to the first-pass effect. Examples of drugs are listed in the Merck Index, Twelfth Ed., Merck Research Laboratories, Whitehouse Station, N.J., 1996, incorporated herein by reference. Determining whether a substance is subject to the first-pass effect is within the skill of the average artisan in this field.

It is preferred that invention materials be protected from stomach acid by, e.g., a coating.

Because adulteration of raw materials is known in the food, flavor, and fragrance industries, citrus-derived components of the invention including cold-pressed citrus oils should preferably be assessed before they are further used in the production of, e.g., compositions of dietary supplements. One strategy consists of sample preparation (Protocol A, this document), followed by chromatography (Protocol B, this document), and ending with comparisons to historical standards. Such assessment can provide consistent batches.

Protocol A: Preparation of Citrus Oils for Administration to Humans by Removal of Toxic, Low Molecular Weight Furocoumarins A volume of cold-pressed citrus oil (Food Chemicals Codex grade) was transferred to a container, and all volatile materials were removed. Although several methods exist for removing volatiles (e.g., distillation, distillation under reduced pressure, evaporation under ambient conditions), the preferred method uses Speed Vac concentrators (Savant Instruments; process requires 12–24 h and pressures of $10^{-2}$–$10^{-3}$ torr, and the system is run without added heat) because this method is gentle and expedient. The nonvolatile product yield is generally 0.04 to 0.1 times the initial volume and is a viscous liquid.

Low molecular weight, phototoxic furocoumarins were removed from the nonvolatile preparation by liquid-liquid extraction: 16 times the volume of viscous liquid of 1:1 ethanol:water (v/v; each U.S.P. grade) were added to the nonvolatile preparation, the container capped, the solution mixed vigorously, the container centrifuged (International Equipment Company, Model K-2, 5 min at setting 35), and the top ethanolic phase discarded. The extraction was repeated twice. Extraneous water and ethanol may be removed from the preparation if desired by use, e.g., of a Speed Vac apparatus. The product of this process may be used for human administration in, e.g., filled capsules.

Protocol B: Chromatography Methods for Processed Citrus Oils

The product of the above Protocol A is not suitable for any high pressure liquid chromatography because of the substantial presence of materials that are not soluble in the preferred mobile phase systems. Hence the sample preparation protocol that follows is used prior to chromatography. One volume of the product of Protocol A is mixed with four volumes of acetonitrile, the container is capped, the solution is mixed vigorously, the container is centrifuged (5 min at setting 35), and the top acetonitrile layer is filtered through a 0.22 micron teflon membrane. The filtered solution is stored in a closed container at −20° C. for 2 days or more and then is passed through filter paper while cold to remove a copious precipitate. The precipitation and filtration step is repeated once. The volume of the acetonitrile solution is noted, and the acetonitrile is removed using a Speed Vac apparatus. The residue is dissolved in half the original volume of acetonitrile, taking care not to disturb any crystalline precipitate, and the solution may now be used for HPLC assessment.

If preparative fractionation of the washed nonvolatile portion of citrus oil is desired, then the HPLC conditions given below are preferred. Linear gradients are used for elution and are formed by mixing mobile phase A composed of water with mobile phase B composed of acetonitrile (instrument: Hewlett Packard). The elution time, in minutes, as well as the percentage of acetonitrile present in the mixed mobile phase are as follows: 0, 75; 5, 75; 10, 90; 11, 98; 17, 98; 18, 75; 22, 75. The chromatographic column has dimensions of 250 mm length×4.6 mm internal diameter, is packed with C18 bonded to 4 micron silica particles (9% carbon load; ODS-L80, YMC, Inc.), is protected with a 23 mm length×4 mm internal diameter column containing the same material and with a 0.5 micron filter, and is maintained at 40+/−0.2° C. The flow rate is maintained at 1.0 mL/min during the 22 min run cycle. The column eluate from each 25 uL injection is monitored at 400+/−200 nm and at 310+/−2 nm and is fractionated using a robotic collector (Gilson).

If qualitative or quantitative assessments of citrus oils, fractions thereof, or reference standards are desired, then the HPLC conditions given below are preferred. Linear gradients are used for elution and are formed by mixing mobile phase A composed of water with mobile phase B composed of acetonitrile (instrument: Hewlett Packard). The elution time, in minutes, as well as the percentage of acetonitrile present in the mixed mobile phase are as follows: 0, 10; 5, 10; 30, 80; 40, 80; 41, 95; 50, 95; 53, 10; 60, 10. The chromatographic column has dimensions of 150 mm length× 2.0 mm internal diameter, is packed with C18 bonded to 4 micron silica particles (14% carbon load; ODS-M80, YMC, Inc.), is protected with a 2 mm internal diameter column packed with a proprietary material (Prism, Keystone Scientific, Inc.) and with a PTFE filter, and is maintained at 35+/−0.2° C. The flow rate is maintained at 0.20 mL/min during the 60 min run cycle. The column eluate from each 10 uL injection is monitored for absorbance at 400+/−200 nm and at 310+/−2 nm and for fluorescence with excitation at 229 nm, emission at 450 nm, and bandpass filtration at 370 nm.

Protocol C: Assessment of Human Cytochrome P450-mediated biotransformation

The process of preparing incubation mixtures begins by mixing 10 uL of ethanol or an ethanolic solution containing an inhibitor with 100 uL of 100 mg/mL bovine serum albumin (Sigma) dissolved in reaction buffer at room temperature. Reaction buffer is composed of 0.10 M sodium phosphate, 1.0 mM ethylenediaminetetraacetic acid, and 5.0 mM magnesium chloride, pH 7.4 (all reagents: Fisher Scientific). Inhibitory chemicals used were ketoconazole (Research Diagnostics, Inc.), miconazole, bergapten, xanthotoxin (previous three from Sigma), bergamotin, imperatorin, isopimpinellin, psoralen, angelicin (previous five from Indofine Chemical Company, Inc.), and fractions or precipitates resulting from Protocols A and B above. When possible, final inhibitor concentrations were expressed in molarity by calculation from the weighed material or by interpolation from HPLC calibration curves prepared with reference materials; otherwise, concentrations are expressed as weight per volume. Reaction tubes are placed on ice in preparation for the manipulations that follow. Sufficient reaction buffer is added so that the final volume of each tube will be 500 uL, 5 uL of a 100-fold concentrate for generating reduced nicotinamide adenine dinucleotide phosphate is added (such that completed reaction mixture contains 1.0 mM nicotinamide adenine dinucleotide phosphate, 1 U/mL glucose-6-phosphate dehydrogenase, and 10 mM glucose-6-phosphate; all from Sigma), and then human hepatic S9 (Anatomic Gift Foundation) is thawed and added in sufficient amounts to cause readily detectable amounts of metabolites to be formed in control reactions (amount necessary varies among individuals, but 10 uL is typical). Reactions are pre-incubated for 3 min at 37° C. in a Dubnoff-type water bath, the reaction mixture is completed by the addition of 10 uL of 100 uM terfenadine (Sigma) dissolved in 1:1 acetonitrile: water and by gentle mixing, the samples are incubated for 15 min at 37° C., and the reaction is stopped by placing the tube on ice and adding 2.5 mL of 300 nM terfenadine-related compound A (internal standard; U. S. Pharmacopeia) dissolved in acetonitrile.

The samples prepared above are readied for HPLC assessment using the protocol that follows. Each tube is vortex mixed and centrifuged for 10 min at setting 35, the resulting supernatant is transferred to a clean tube, and the liquid is evaporated using a Speed Vac apparatus. The residue in each tube is first dissolved in 40 uL 1:1 acetonitrile:water, 2.5 mL of acetonitrile is added, and the centrifuge-transfer-evaporate step just described is repeated.

The dry residue resulting from the above-described experiments and sample preparation protocol may be analyzed for terfenadine metabolites using the HPLC method described below and may also be used to quantitate the inhibitory chemicals that were added to the reaction (see Protocol B). Linear gradients are used for elution and are formed by mixing mobile phase A composed of water with mobile phase B composed of 0.025% (v/v) formic acid in acetonitrile (instrument: Hewlett Packard). The elution time, in minutes, the percentage of mobile phase B present in the mixed mobile phase, and the flow rate (mL/min) are as follows: 0, 10, 0. 10; 2, 10, 0.10; 3.5, 10, 0.20; 4, 10, 0.25; 5, 10, 0.25; 30, 55, 0.25; 32, 98, 0.25; 33, 98, 0.40; 39.8, 98, 0.40; 40, 98, 0.25; 45, 10, 0.25; 45.25, 10, 0.20; 50, 10, 0.20; 50.25, 10, 0.10. The chromatographic column has dimensions of 150 mm length×2.1 mm internal diameter, is packed with a proprietary material (Prism, Keystone Scientific, Inc.), is protected with a 2 mm internal diameter column containing the same material and with a PTFE filter, and is maintained at 35+/−0.2° C. The dry sample residue is mixed with 60 uL of 1:1 acetonitrile:water followed by 40 uL water just prior to each 50.25 min run cycle. The column eluate from each 10 uL injection is monitored for fluorescence with excitation at 228 nm, emission at 291 nm, and bandpass filtration at 280 nm. Under these conditions, the retention times of terfenadine alcohol metabolite, terfenadine carboxylic acid metabolite, and the internal standard are 16.2 min, 17.4 min, and 22.2 min, respectively.

As mentioned above, because adulteration of raw materials is known in the flavor and fragrance industry, cold-pressed citrus oils should be assessed before they are used for production. Another assessment strategy, particularly useful for isolation of invention fractions, consists of sample preparation (Protocol A', this document), followed by chromatography (Protocol B', this document), and optionally ending with comparisons to historical standards. Preferred methodology is described in Protocols A"–C" and D' below.

Protocol A': Pretreatment of Citrus Oils Prior to Chromatography

Most citrus oils are not directly suitable for long-term preparative high pressure liquid chromatography because of the substantial presence of materials that show poor solubility in the preferred mobile phase systems. Hence the sample preparation protocol that follows is used prior to chromatography.

Cold-pressed citrus oil (Food Chemicals Codex grade) is transferred to a suitable container, and all volatile materials are removed under reduced pressure ($10^{-2}$–$10^{-3}$ torr, 3–4 days). The nonvolatile product yield is generally only 5–10% of the original volume. The citrus nonvolatiles are mixed with acetonitrile in a ratio of 2:1 (w/w), the mixture is centrifuged (International Equipment Company, Model K-2, 5 min at setting 35), and the upper acetonitrile-containing phase is removed. The extraction with acetonitrile is repeated once, the lower phase is discarded, the first and second acetonitrile phases are pooled, and acetonitrile is removed using Speed Vac concentrators (Savant Instruments; 12 h at $10^{-2}$–$10^{-3}$ torr, without added heat). The nonvolatile material is mixed with ethanolic base (1:1 ethanol:water {v/v; each U.S.P. grade} containing 12.5 g potassium hydroxide/L) in a ratio of 1:4 (w/v), the mixture is centrifuged for 5 min at setting 35, and the upper ethanolic phase is removed and discarded. The nonvolatile material is washed an additional nine times with ethanolic base and, then, once with 1:1 ethanol:water (v/v). The residue that remains is extracted twice with sufficient volumes of acetonitrile such that all colored material is removed. The acetonitrile solution is washed six times with two volumes of hexane, with each hexane extract (upper layer) being removed and discarded, and the resulting acetonitrile solution is filtered through a 0.2 micron teflon membrane and evaporated to dryness using a Speed Vac concentrator.

The final product of the above process should appear as a viscous, deep red oil, but seasonal variations in the starting material (citrus oils) apparently can change the quality and appearance of the product of the above process. Hence, if a copious orange crystalline material contaminates the deep red oil, then the number of additional washes with ethanolic base should be increased from nine to nineteen.

Protocol B': Chromatography Methods for Processed Citrus Oils

If preparative fractionation of the washed nonvolatile portion of citrus oil (product of Protocol A') is desired, then the HPLC conditions given below are preferred. Linear gradients are used for elution and are formed by mixing mobile phase A composed of water with mobile phase B composed of acetonitrile (instrument: Hewlett Packard). The elution time, in minutes, as well as the percentage of acetonitrile present in the mixed mobile phase are as follows: 0, 75; 5, 75; 10, 90; 11, 98; 17, 98; 18, 75; 22, 75. The chromatographic column has dimensions of 250 mm length× 4.6 mm internal diameter, is packed with C18 bonded to 4 micron silica particles (9% carbon load; ODS-L80 YMC, Inc.), is protected with a 23 mm length×4 mm internal diameter column containing the same material and with a 0.5 micron filter, and is maintained at 40+/−0.2° C. The flow rate is maintained at 1.0 mL/min during the 22 min run cycle. The column eluate from each 25 uL injection of oil obtained by Protocol A' is monitored at 400+/−200 nm and at 310+/−2 nm and is fractionated using a robotic collector (Gilson).

If qualitative or quantitative assessments of citrus oils, fractions thereof, or reference standards are desired, then the HPLC conditions given below are preferred. Linear gradients are used for elution and are formed by mixing mobile phase A composed of water with mobile phase B composed of acetonitrile (instrument: Hewlett Packard). The elution time, in minutes, as well as the percentage of acetonitrile present in the mixed mobile phase are as follows: 0, 10; 5, 10; 30, 80; 40, 80; 41, 95; 50, 95; 53, 10; 60, 10. The chromatographic column has dimensions of 150 mm length× 2.0 mm internal diameter, is packed with C18 bonded to 4 micron silica particles (14% carbon load; ODS-M80, YMC, Inc.), is protected with a 2 mm internal diameter guard column packed with a proprietary material (Prism, Keystone Scientific, Inc.) and with a PTFE filter, and is maintained at 35+/−0.2° C. The flow rate is maintained at 0.20 mL/min during the 60 min run cycle. The column eluate from each 10 uL injection is monitored for absorbance at 400+/−200 nm and at 310+/−2 nm and for fluorescence with excitation at 229 nm, emission at 450 nm, and bandpass filtration at 370 nm.

Protocol D': Assessment of Human Cytochrome P450-mediated Biotransformation

The process of preparing incubation mixtures begins by mixing 10 uL of ethanol (control reactions) or an ethanolic solution containing an inhibitor with 100 uL of 100 mg/mL bovine serum albumin (Sigma) dissolved in reaction buffer at room temperature. Reaction buffer is composed of 0.10 M sodium phosphate, 1.0 mM ethylenediaminetetraacetic acid, and 5.0 mM magnesium chloride, pH 7.4 (all reagents: Fisher Scientific). Inhibitory chemicals used are ketoconazole (Research Diagnostics, Inc.), ritonavir (Norvir™, Abbott Laboratories), and fractions resulting from Protocols B', B" and C'. Final inhibitor concentrations were expressed in molarity by calculation from the weighed material or by use of Beer's law. Reaction tubes are placed on ice in preparation for the manipulations that follow. Sufficient reaction buffer is added so that the final volume of each tube will be 500 uL, 5 uL of a 100-fold concentrate for generating reduced nicotinamide adenine dinucleotide phosphate is added (such that completed reaction mixture contains 1.0 mM nicotinamide adenine dinucleotide phosphate, 1 U/mL glucose-6-phosphate dehydrogenase, and 10 mM glucose-6-phosphate; all from Sigma), and then human hepatic S9 (Anatomic Gift Foundation) is thawed and added in sufficient amounts to cause readily detectable amounts of metabolites to be formed in control reactions (amount necessary varies among individuals, but 10 uL is typical). Reactions are pre-incubated for 3 min at 37° C. in a Dubnoff-type water bath, the reaction mixture is completed by the addition of 10 uL of 500 uM saquinavir (Invirase™, Roche Laboratories) dissolved in 1:1 ethanol:water and by gentle mixing, the samples are incubated for 15 min at 37° C., and the reaction is stopped by placing the tube on ice and adding 2.5 mL of acetonitrile.

The samples prepared above are readied for HPLC assessment using the protocol that follows. Each tube is vortex mixed and centrifuged for 10 min at setting 35, the resulting supernatant is transferred to a clean tube, and the liquid is evaporated using a Speed Vac apparatus. The residue in each tube is first dissolved in 40 uL 1:1 acetonitrile:water, 2.5 mL of acetonitrile is added, and the centrifuge-transfer-evaporate step just described is repeated.

The dry residue resulting from the above-described experiments and sample preparation protocol may be analyzed for saquinavir and saquinavir metabolites using the HPLC method described below and may also be used to quantitate the inhibitory chemicals that were added to the reaction (see Protocol B'). Linear gradients are used for elution and are formed by mixing mobile phase A composed of water with mobile phase B composed of acetonitrile (instrument: Hewlett Packard). The elution time, in minutes, and the percentage of mobile phase B present in the mixed mobile phase are as follows: 0, 10; 5, 10; 30, 80; 31, 95; 40, 95; 43, 10; 48, 10. The flow rate is 0.2 mL/min throughout the run. The chromatographic column has dimensions of 150 mm length×2.1 mm internal diameter, is packed with a proprietary material (Prism, Keystone Scientific, Inc.), is protected with a 2 mm internal diameter column containing the same material and with a PTFE filter, and is maintained at 35+/−0.2° C. In order to minimize the degradation of analytes, the dry sample residue is mixed with 50 uL of 1:1 acetonitrile:water just prior to each 48 min run cycle. The column eluate from each 10 uL injection is monitored for absorbance at 239+/−2 nm. Under these conditions, the retention times of saquinavir principal metabolite A, saquinavir principal metabolite B, and saquinavir are 24.2 min, 26.0 min, and 30.0 min, respectively.

Protocol A": Pretreatment of Citrus Oils Prior to Chromatography

Most citrus oils are not directly suitable for long-term preparative high pressure liquid chromatography because of the substantial presence of materials that show poor solubility in the preferred mobile phase systems. Hence the sample preparation protocol that follows is used prior to chromatography.

Cold-pressed citrus oil (Food Chemicals Codex grade) is transferred to a suitable container, and all volatile materials are removed under reduced pressure ($10^{-2}$–$10^{-3}$ torr, 3–4 days). The nonvolatile product yield is generally only 5–10% of the original volume. The citrus nonvolatiles are mixed with acetonitrile in a ratio of 2:1 (w/w), the mixture is centrifuged (International Equipment Company, Model K-2, 5 min at setting 35), and the upper acetonitrile-containing phase is removed. The extraction with acetonitrile is repeated once, the lower phase is discarded, the first and second acetonitrile phases are pooled, and acetonitrile is removed using Speed Vac concentrators (Savant Instruments; 12 h at $10^{-2}$–$10^{-3}$ torr, without added heat). The nonvolatile material is mixed with ethanolic base (1:1 ethanol:water {v/v; each U.S.P. grade} containing 12.5 g potassium hydroxide/L) in a ratio of 1:4 (w/v), the mixture is centrifuged for 5 min at setting 35, and the upper ethanolic phase is removed and discarded. The nonvolatile material is washed an additional nine times with ethanolic base and, then, once with 1:1 ethanol:water (v/v). The residue that remains is extracted twice with sufficient volumes of acetonitrile such that all colored material is removed. The acetonitrile solution is washed six times with two volumes of hexane, with each hexane extract (upper layer) being removed and discarded, and the resulting acetonitrile solution is filtered through a 0.2 micron teflon membrane and evaporated to dryness using a Speed Vac concentrator.

The final product of the above process should appear as a viscous, deep red oil, but seasonal variations in the starting material (citrus oils) apparently can change the quality and appearance of the product of the above process. Hence, if a copious orange crystalline material contaminates the deep red oil, then the number of additional washes with ethanolic base should be increased from nine to nineteen.

Protocol B": Chromatography Methods for Processed Citrus Oils

The HPLC conditions given below are preferred for preparative fractionation of the washed nonvolatile portion of citrus oil (product of Protocols A, A' or A"). Linear gradients are used for elution and are formed by mixing mobile phase A composed of water with mobile phase B composed of acetonitrile (instrument: Hewlett Packard). The elution time, in minutes, as well as the percentage of acetonitrile present in the mixed mobile phase are as follows: 0, 75; 5, 75; 10, 90; 11, 98; 17, 98; 18, 75; 22. 75. The chromatographic column has dimensions of 250 mm length× 4.6 mm internal diameter, is packed with C18 bonded to 4 micron silica particles (9% carbon load; YMC. Inc.), is protected with a 23 mm length×4 mm internal diameter column containing the same material and with a 0.5 micron filter, and is maintained at 40+/−0.2° C. The flow rate is maintained at 1.0 mL/min during the 22 min run cycle. The column eluate from each 25 uL injection is monitored at 400+/−200 nm and at 310+/−2 nm and is fractionated using a robotic collector (Gilson).

Protocol C": Purification of Inhibitor Fractions (of Human Cytochrome P450-mediated biotransformation) 01, 02, 03, 04, 05, and 06 Using a Chiral HPLC Column Pooled residues that result from fractionation of the 11–12.5 min region (Protocol B, B' or B") and solvent removal (Speed Vac, no heat added) are subjected to chiral chromatography. Isocratic elution is employed (mobile phase consists of 3.4 L isooctane, 0.6 L 95% ethanol {remainder is water}, and 0.2 L isopropanol) to elute Inhibitor fractions 01–06 from the column (250×4.6 mm, Keystone Scientific, Inc., Chiral DNB {S}) in less than 34 min (instrument: Hewlett Packard). The flow rate is maintained at 1.0 mL/min and the column is kept at 40+/−0.2° C. The column eluate from each 25 uL injection (residue is dissolved in mobile phase) is monitored at 400+/−200 nm and at 310+/−2 nm and is fractionated using a robotic collector (Gilson).

Isolation of Fractions X4 and Z12

The two preferred fractions were isolated as follows: Grapefruit oil is prepared according to Protocol A' or A" above and the product is purified according to Protocol B, B' or B" (preparative section). Fraction X4 elutes in the Protocol B' preparative scheme at 11.6–11.7 minutes and Fraction Z12 elutes at 12.4–12.5 minutes.

Figure 1:
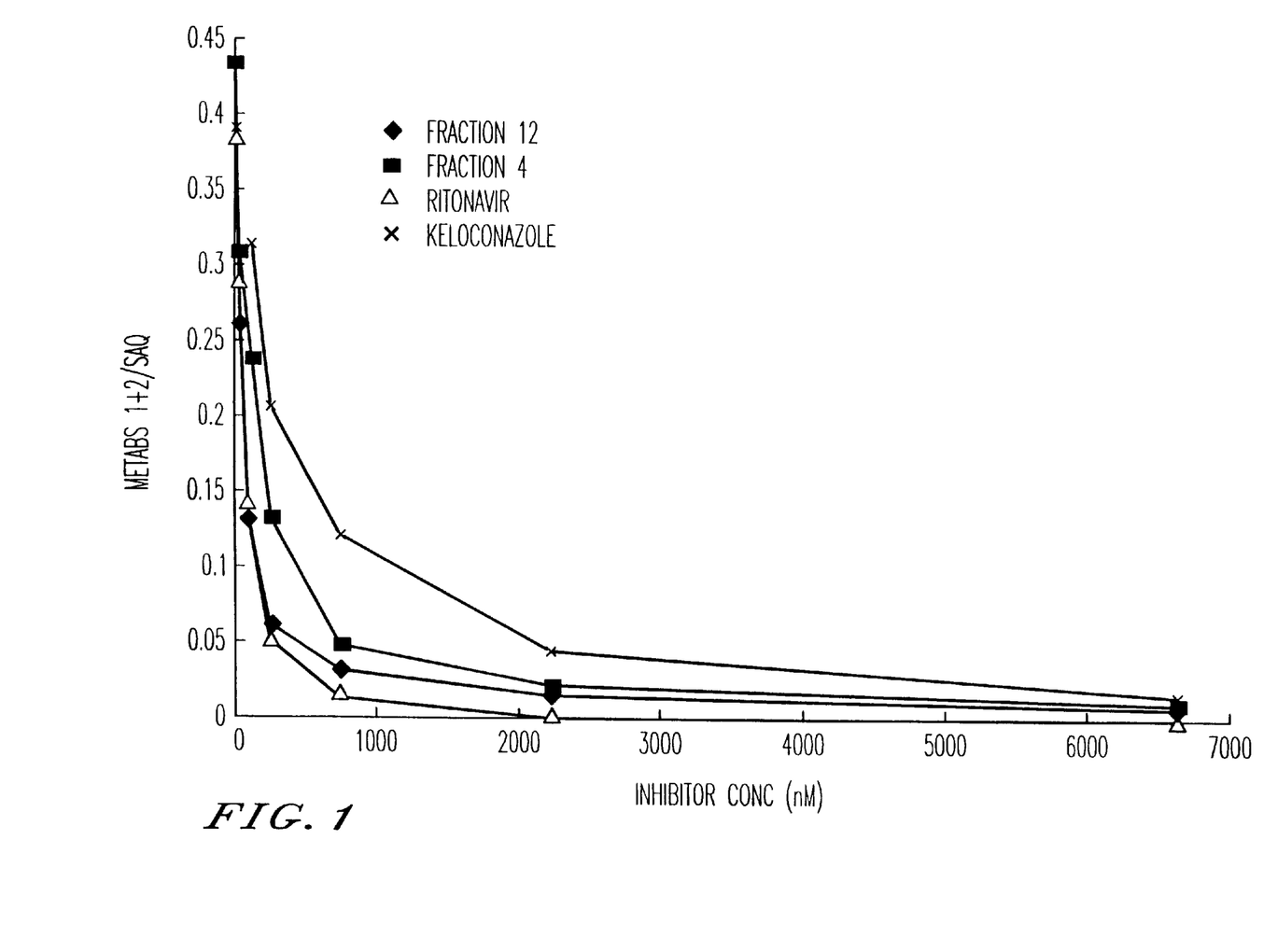
FIG. 1 shoes the first-pass effectiveness X4 and Z12.

First-pass effectiveness of fractions X4 and Z12 are shown in FIG. 1, along with known bioenhancers ketoconazole and ritonavir, and are denoted fraction 4 and fraction 12, respectively (conducted according to Protocol D' above). UV, $^{13}$C NMR (CD$_3$OD), $^1$H NMR (CD$_3$OD) and mass spectral data of fractions X4 and Z12 (FAB MS, electron impact MS and electrospray MS) were taken.

Isolation of Inhibitors 01–04 from Fraction X4

Figure 2:
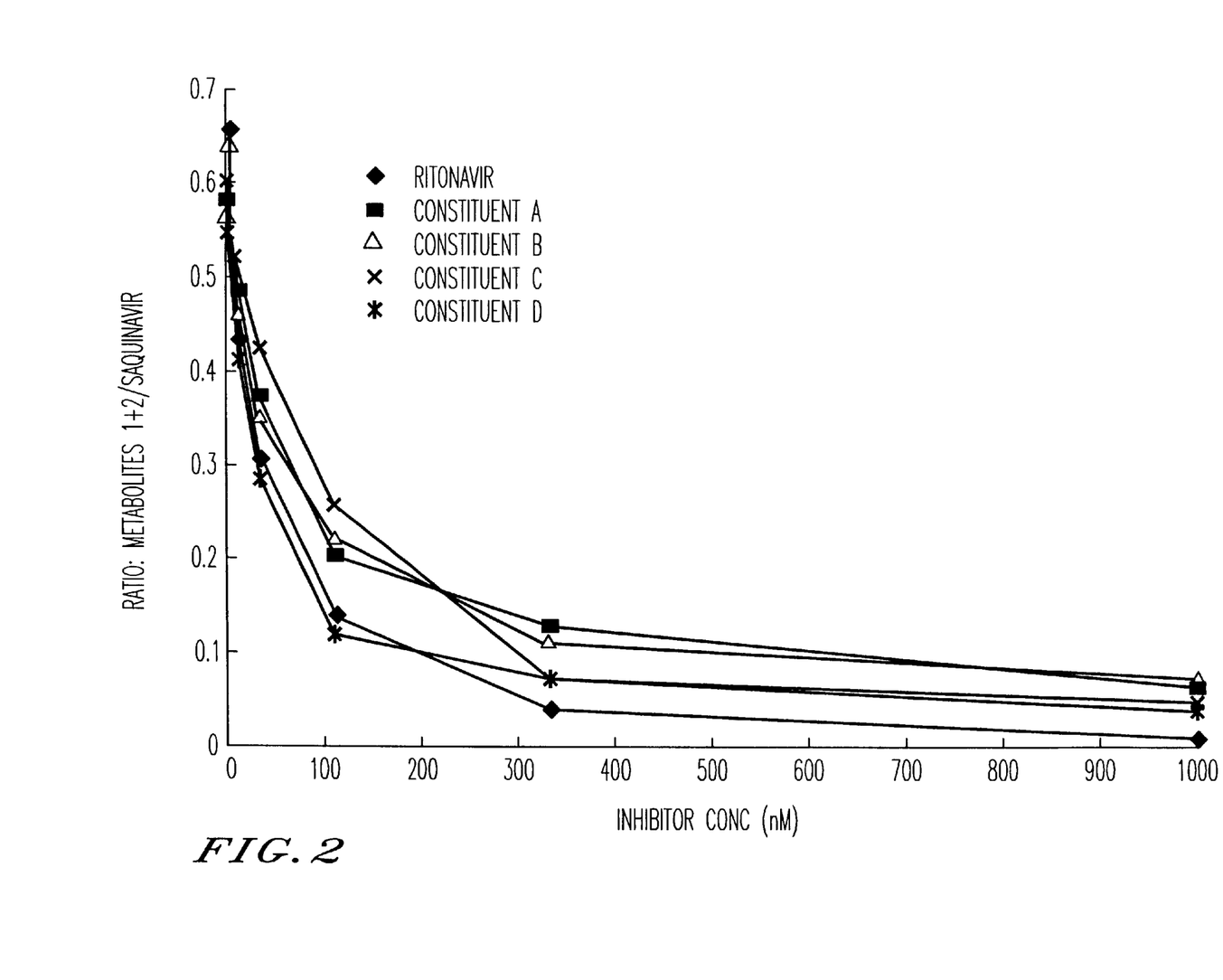
FIG. 2 shows the first-pass effectiveness of constituents A–D.

Fraction X4 described above is subjected to Protocol C" to provide Inhibitors 01–04. These Inhibitors were tested according to Protocol D'. The results are shown in FIG. 2 where Inhibitors 01–04 are noted A–D respectively.

Figure 3A:
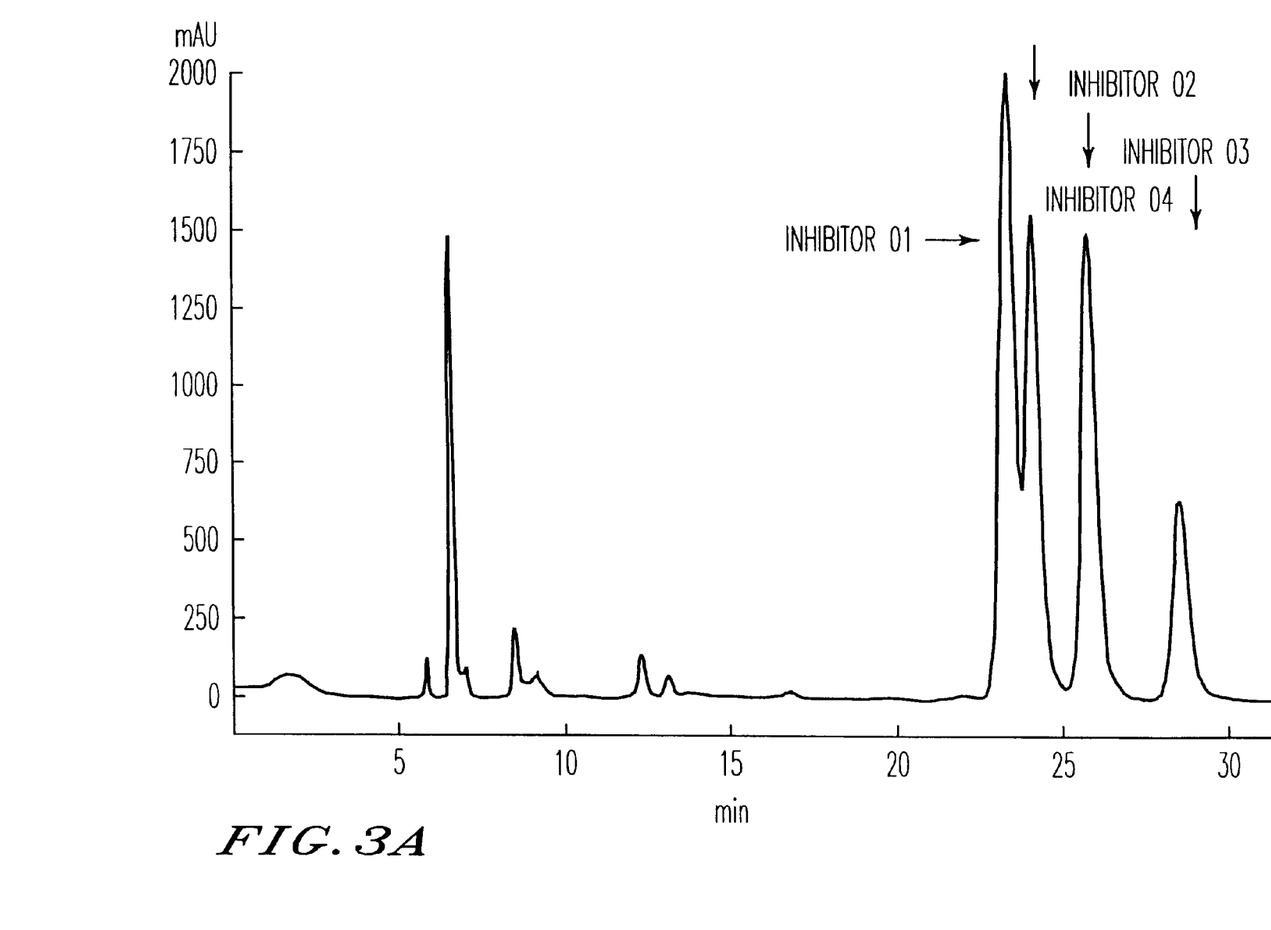
FIG. 3 and 4 show chiral chromatograms of fractions X4 and Z12, and identify specific inhibitors.
Figure 3B:
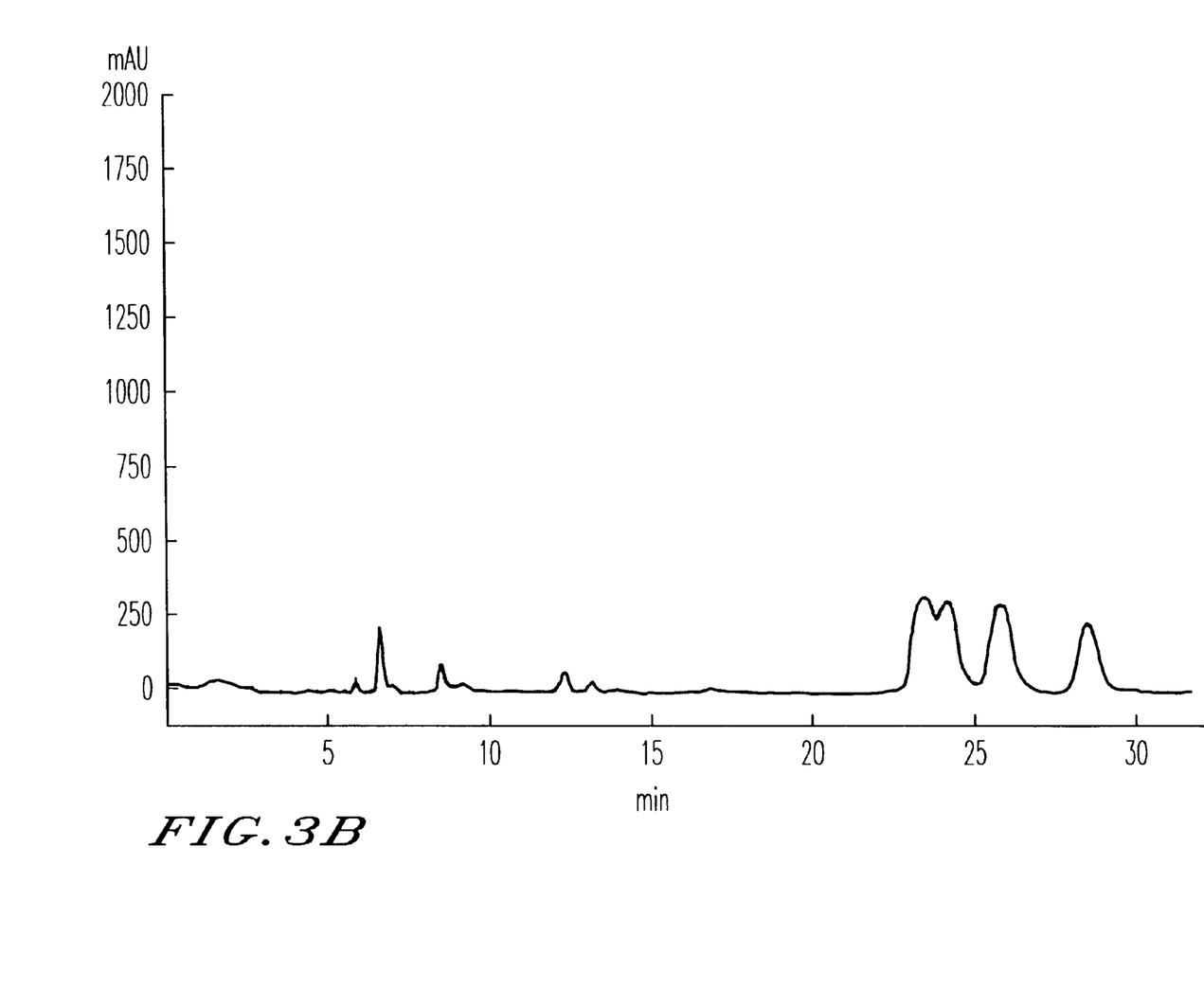
Figure 4A:
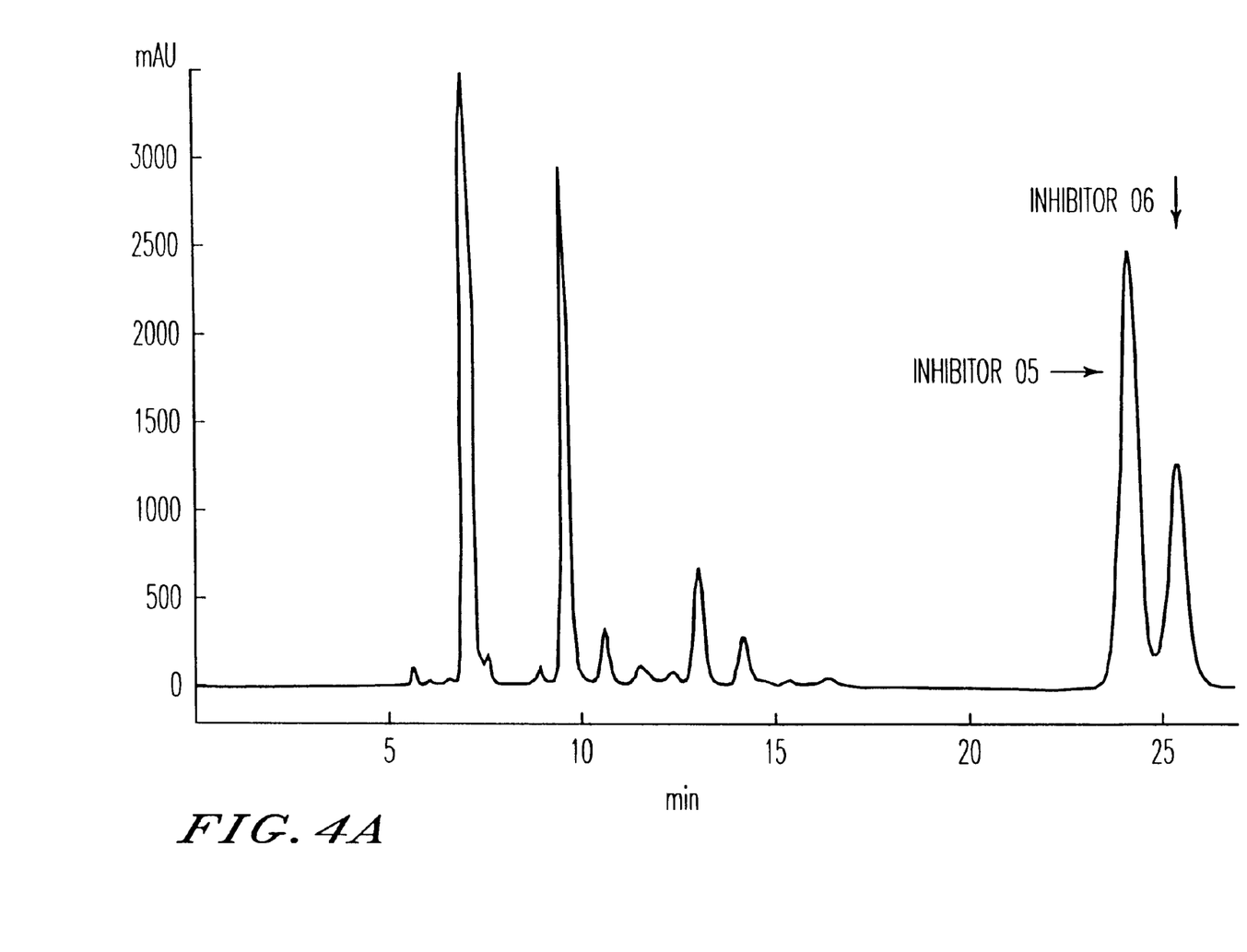
Figure 4B:
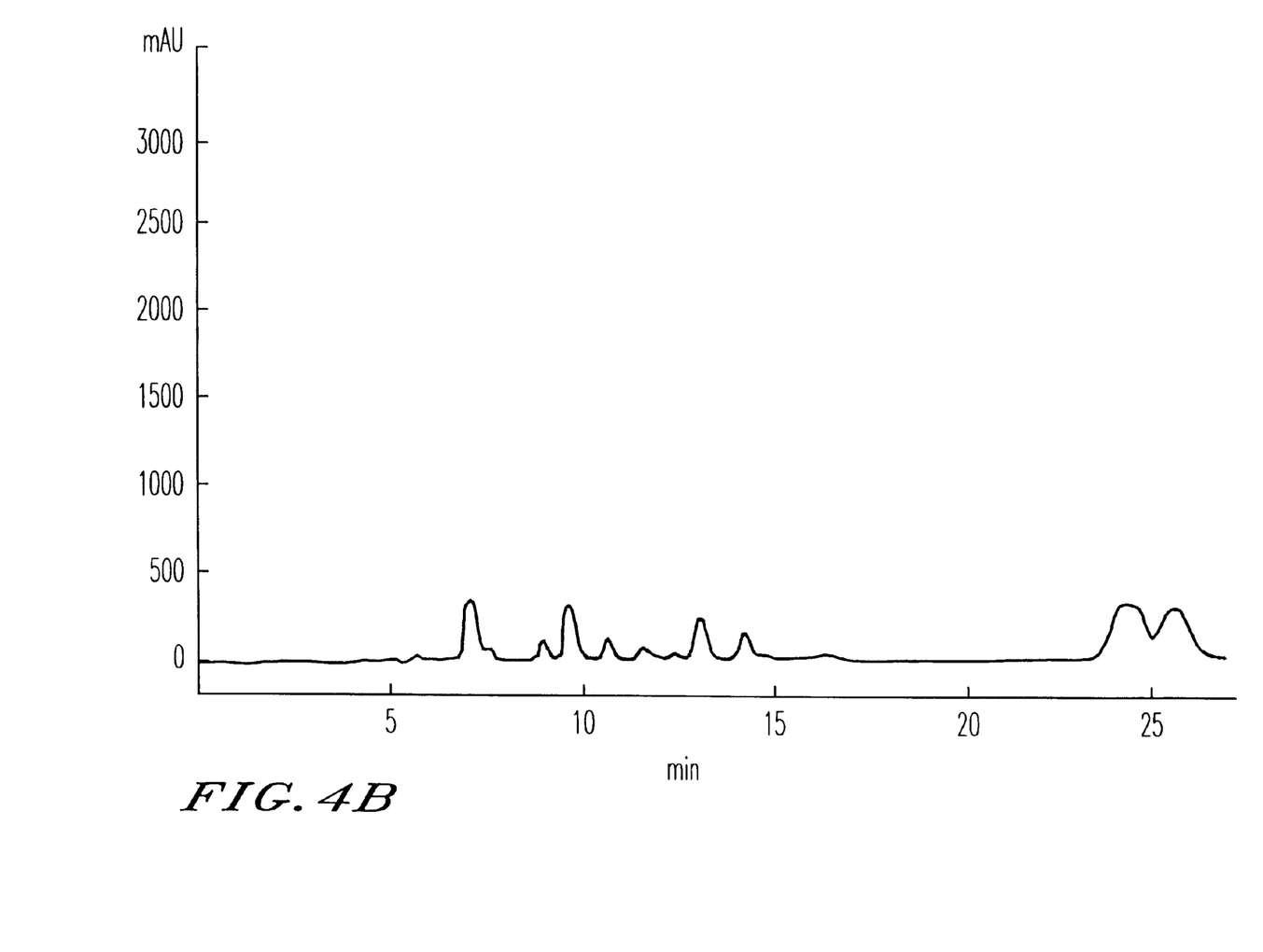

Chiral chromatograms of fractions X4 and Z12 are shown in FIGS. 3 and 4 where fractions 01–06 are identified. Note Protocol C" above.

Isolation of Inhibitors 05 and 06 from Fraction Z12

Fraction Z12 described above is subjected to Protocol C" above to provide Inhibitors 05 and 06.

With regard to purification and processing methods, the following embodiments are preferred:

1. A method for processing citrus and selectively removing phototoxic furocoumarins from a first-pass effective citrus-derived substance, comprising the step of extracting said citrus-derived substance with a mixture of at least one $C_2$–$C_4$ alcohol and water, said first-pass effective citrus-derived substance maintaining anti-first-pass activity after said extraction.

2. The method of embodiment 1, wherein said citrus-derived substance is a cold-pressed citrus oil.

3. The method of embodiment 1, wherein said mixture of ethanol and water is a 1:1 volume/volume mixture of ethanol and water.

Other preferred embodiments include:

4. A first-pass effective citrus-derived substance which has been extracted with a mixture of at least one $C_2$–$C_4$ alcohol and water so as to reduce the amount of phototoxic furocoumarins therein.

5. The citrus-derived substance of embodiment 4, wherein said substance is a cold-pressed citrus oil.

6. The citrus-derived substance of embodiment 4, which has been extracted with a 1:1 volume/volume mixture of ethanol and water.

7. A method for inhibiting the first-pass-effect of a material taken orally by a patient which is subject to the first-pass effect, comprising the step of co-administering to said patient the first-pass effective citrus-derived substance of embodiment 4.

Invention compositions comprising invention inhibitor material (fractions, etc.) (e.g., alone, mixed with drug(s), and/or diluent(s) and/or carrier(s) etc.) preferably comprise enough material such that they inhibit saquinavir biotransformation according to Protocol D' above better than pure ketoconazole on an equal molar or weight concentration basis. Alternatively, invention compositions preferably provide a Y-axis value in Protocol D' (see FIG. 1) of less than 0.5, preferably 0.45, 0.4, 0.35, 0.3, 0.25, 0.22, 0.2, 0.18, 0.15, 0.12, 0.1, 0.08, 0.05 or 0.03 or less when 0.01–0.25 mg, including 0.02, 0.04, 0.06, 0.08, 0.1, 0.12, 0.14, 0.16, 0.18, 0.2, 0.22 and 0.24, and all ranges between all values, of composition are diluted or dissolved to one liter.

U.S. application Ser. Nos. 09/001,218, 08/997,259 (Docket No. 7552-0008-99 filed Dec. 23, 1997), 08/673,800, 60/056,382 and 60/048,183 are incorporated herein by reference.

What is claimed is:

1. A process comprising:

1. providing an oil of a first-pass citrus,
2. removing volatile materials in said oil by subjecting said oil to evaporation, distillation or reduced pressure to provide a residue,
3. extracting said residue with acetonitrile and evaporating said acetonitrile to provide an acetonitrile-soluble semi-purified residue,
4. washing said semi-purified residue with an ethanol-water mixture optionally containing base to provide a washed semi-purified residue,
5. extracting said washed semi-purified residue with acetonitrile to provide an acetonitrile solution,
6. washing said acetonitrile solution with an alkane solvent and evaporating acetonitrile from said acetonitrile solution to provide a purified residue,
7. subjecting said purified residue to reverse phase HPLC to provide plural fractions at least one of which is a primary first-pass effective fraction,
8. optionally subjecting said primary first-pass effective fraction to chiral HPLC to provide plural fractions at least one of which is a secondary first-pass effective fraction.

2. The process of claim 1, wherein said primary first-pass effective fraction is subjected to chiral HPLC to provide plural fractions at least one of which is a secondary first-pass effective fraction.

* * * * *